United States Patent
Kojima et al.

[11] Patent Number: 5,849,165
[45] Date of Patent: Dec. 15, 1998

[54] OXYGEN SENSOR FOR PREVENTING SILICON POISONING

[75] Inventors: Takao Kojima; Hiroyuki Ishiguro, both of Nagoya; Masaru Yamano, Komaki; Toshiki Sawada, Nagoya; Kazuo Taguchi, Nagoya; Masahiko Yamada, Nagoya; Noriaki Kondo, Ichinomiya, all of Japan

[73] Assignee: NGK Spark Plug Co. Ltd., Nogoya, Japan

[21] Appl. No.: 408,132

[22] Filed: Mar. 21, 1995

Related U.S. Application Data

[63] Continuation of Ser. No. 190,567, Feb. 2, 1994, abandoned, which is a continuation of Ser. No. 834,985, Feb. 14, 1992, abandoned, which is a continuation of Ser. No. 429,946, Nov. 1, 1989, abandoned.

[30] Foreign Application Priority Data

| Nov. 1, 1988 | [JP] | Japan | 63-276743 |
| Nov. 1, 1988 | [JP] | Japan | 63-276744 |
| Nov. 2, 1988 | [JP] | Japan | 63-276302 |
| Dec. 28, 1988 | [JP] | Japan | 63-328993 |
| Mar. 17, 1989 | [JP] | Japan | 1-63942 |
| Sep. 29, 1989 | [JP] | Japan | 1-252025 |

[51] Int. Cl.$^6$ .......................... G01N 27/12; G01N 27/41; G01N 27/409
[52] U.S. Cl. .......................... 204/429; 204/424; 204/425; 204/426; 204/427; 205/784.5; 205/785; 422/98; 427/126.1; 427/402; 427/419.1; 427/443.2
[58] Field of Search ...................... 204/153.18, 421–429; 205/783.5, 784, 784.5, 785; 422/98

[56] References Cited

U.S. PATENT DOCUMENTS

| 3,202,596 | 8/1965 | Canevari | 204/197 |
| 3,929,588 | 12/1975 | Parker et al. | 204/415 |
| 3,989,614 | 11/1976 | Tien | 204/426 |
| 3,997,419 | 12/1976 | Scott et al. | 204/415 |
| 4,021,326 | 5/1977 | Pollner et al. | 204/429 |

(List continued on next page.)

FOREIGN PATENT DOCUMENTS

| A-0 331 513 | 6/1989 | European Pat. Off. . |
| 55-20623 | 2/1980 | Japan . |
| 57-34900 | 7/1982 | Japan . |
| 59-222754 | 12/1984 | Japan . |
| 61-79155 | 4/1986 | Japan . |
| 62-245148 | 10/1987 | Japan . |
| 64-458 | 1/1989 | Japan . |
| 64-83150 | 3/1989 | Japan . |

OTHER PUBLICATIONS

*Handbook of Chemistry and Physics*, 55th ed., 1974–1975, pp. B–105 and B106.
English Abstract of DE–A–2656648, Jun. 23, 1977.
Hackh's Chemical Dictionary, (1969) Month Unavailable, pp. 327, 651, 659, 725.
Hackh's Chemical Dictionary, 4th ed. (1969) Month Unavailable, p. 687.
Patent Abstracts of Japan, vol. 13, No. 337 (P–906), 28th Jul. 1989; JP–A–01 097 855 (NGK Spark Plug Co., Ltd.) 17 Apr. 1989.
Patent Abstracts of Japan, vol. 8, No. 233 (P–309) [1670], 26th Oct. 1984; JP–A–59 109 854 (Mazda K.K.) 25 Jun. 1984.

*Primary Examiner*—T. Tung
*Attorney, Agent, or Firm*—Fish & Richardson P.C.

[57] ABSTRACT

Oxygen sensor element ($ZrO_2$ solid electrolyte etc) for detecting oxygen concentration in an exhaust gas has a protective layer which is made of a heat-resistant metal oxide and which carries a component of a IIa subgroup element (Ca, Mg etc) on the side exposed to the exhaust gas of the sensor element, at least a part of the protective layer being present as a nonstoichiometric compound (Ti oxide etc) with respect to the heat-resistant metal oxide. Si-poisoning is prevented. Heater for heating the sensor element is provided for preventing Si-poisoning at low temperatures.

17 Claims, 10 Drawing Sheets

U.S. PATENT DOCUMENTS

| | | |
|---|---|---|
| 4,272,349 | 6/1981 | Furutani . |
| 4,280,890 | 7/1981 | Friese et al. . |
| 4,296,148 | 10/1981 | Friese ........................................ 204/426 |
| 4,297,192 | 10/1981 | Shinohara . |
| 4,402,820 | 9/1983 | Sano . |
| 4,502,939 | 3/1985 | Holfelder et al. ....................... 204/427 |
| 4,535,316 | 8/1985 | Wertheimer et al. ...................... 422/98 |
| 4,556,475 | 12/1985 | Bayha et al. ............................ 204/427 |
| 4,608,232 | 8/1986 | Sunano et al. ............................ 422/98 |
| 4,701,739 | 10/1987 | Sasaki ....................................... 422/98 |
| 4,720,335 | 1/1988 | Fukushima et al. ..................... 204/427 |
| 4,851,105 | 7/1989 | Ishiguro et al. ......................... 204/429 |
| 4,915,080 | 4/1990 | Nakaniwa et al. ...................... 204/426 |

SENSOR OUTPUT

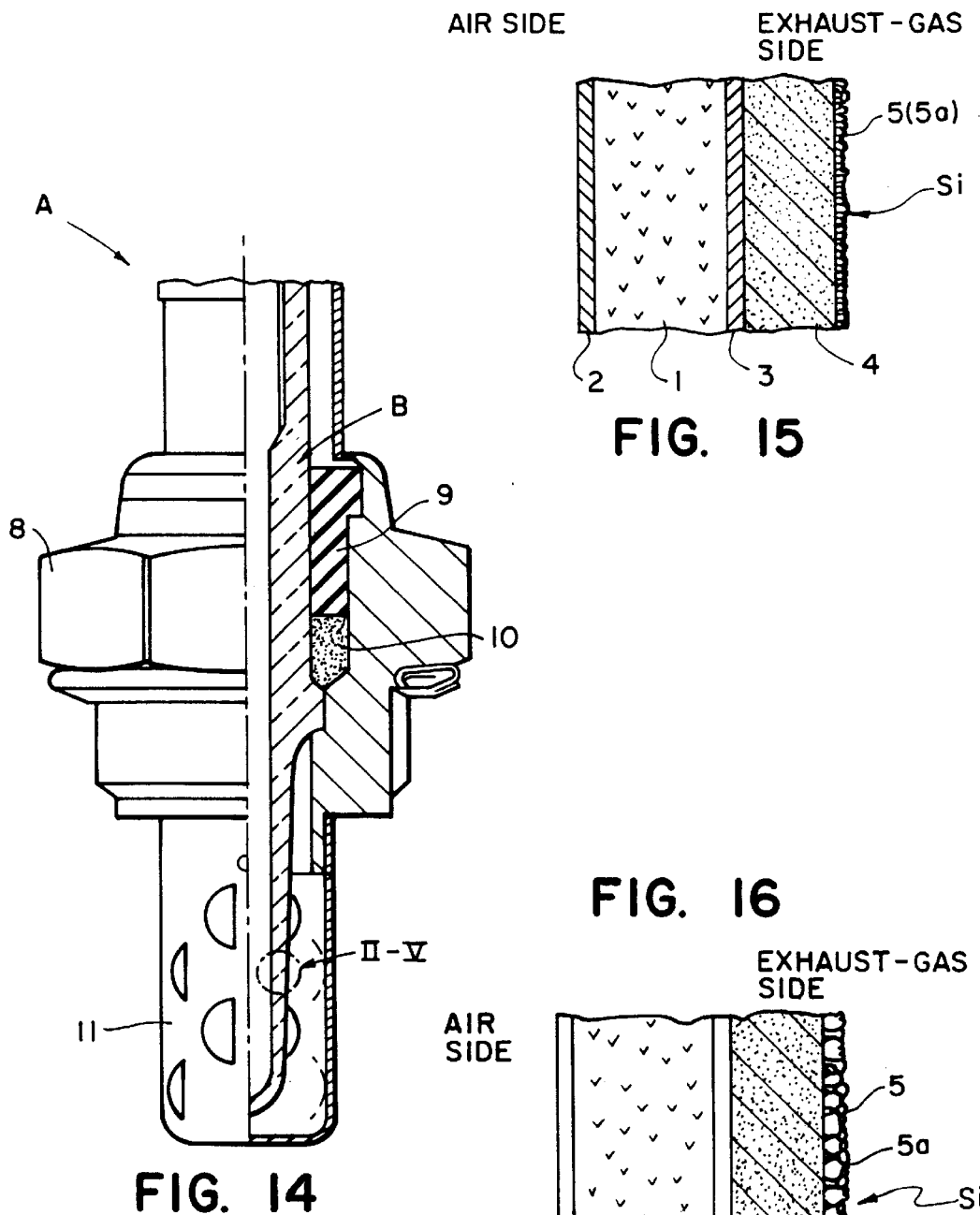
FIG. 14
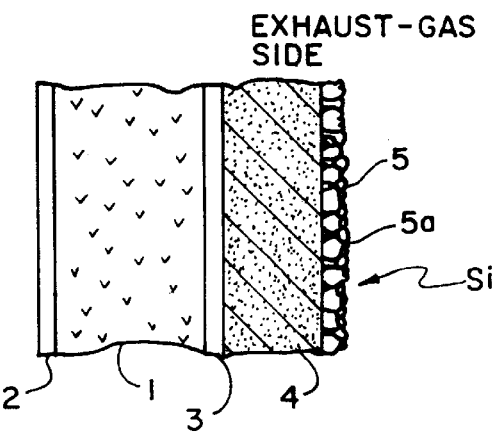
FIG. 15
FIG. 16

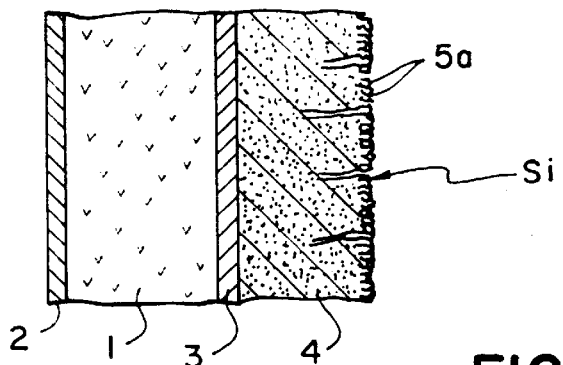
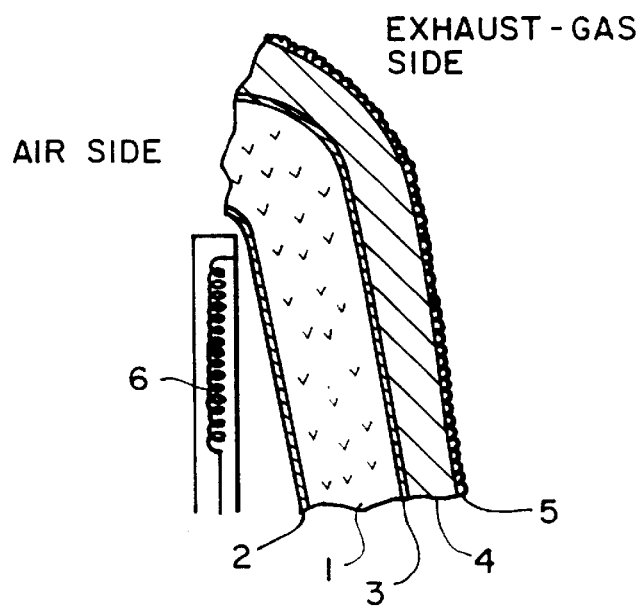
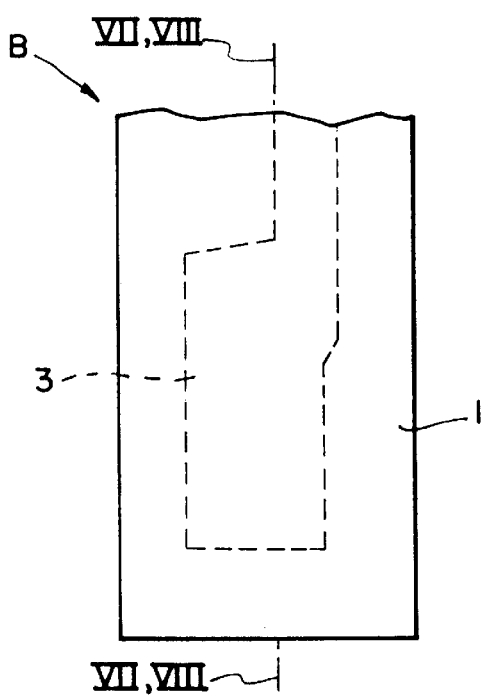

- GREEN SHEET PRINTED WITH ELECTRODES
- GREEN SHEET FOR SPACER
- GREEN SHEET FOR OPPOSITE MEMBER

OXYGEN SENSOR FOR PREVENTING SILICON POISONING

This application is a continuation of U.S. application Ser. No. 08/190,567, filed Feb. 2, 1994, now abandoned, which is a continuation of U.S. application Ser. No. 07/834,985, filed Feb. 14, 1992, now abandoned, which is a continuation of U.S. application Ser. No. 07/429,946, filed Nov. 1, 1989, now abandoned.

FIELD OF THE INVENTION

This invention relates to an oxygen sensor, and more particularly, to an oxygen sensor for controlling air/fuel ratio which is utilized in combination with a three-way catalyst in an exhaust-gas purification system for automobiles and the like.

BACKGROUND

Environment surrounding oxygen sensors is rather severe. Regulation for exhaust gases is being intensified. Especially, $NO_x$ regulation of 0.4 g/mile or less has already been enforced in California. Hence, there become important prerequisites for sensors to suppress variations in initial control air/fuel ratio (A/F ratio) and variations in A/F ratio after application for a long period of time.

Recently, in addition, materials including silicon are mostly being used for engine parts (e.g., packings), and the influence due to the presence of the silicon in exhaust gases cannot be ignored for the sensor.

SUMMARY OF THE DISCLOSURE

Accordingly, it is an object of the present invention to prevent variations in the initial control A/F ratio, to minimize variations in the A/F ratio after application for a long period of time, and to prevent shift to the lean side due to Si poisoning and deterioration in fall response property.

In order to suppress variations in the initial control A/F ratio and variations in the A/F ratio after applications for a long period of time, various kinds of countermeasures have been performed in which a noble metal is included within an exhaust-gas-side protective layer of an oxygen sensor in order to complete combustion reaction of unburnt components until a gas reaches a sensor electrode. Among them, the present applicant also found that by providing a protective layer (a second protective layer) made of a nonstoichiometric compound, it is possible to hold a catalyst which has a very strong effect even after durability tests (JP Patent Application No. 62-311278 (1987), now JP Patent Kokai Publication No. 1-97855 (1989)and the subject matter of a parallel U.S. patent application Ser. No. 429,944). In this invention, particles made of a nonstoichiometric compound, for example, $TiO_{2-x}$ ($x \leq 0.4$), have electron holes or defects, prevent the adsorption of excessive CO and $O_2$ on electrodes and/or protective layer in rich/lean atmospheres, and are adapted well to noble metals. Hence, it becomes possible to concentrate the initial control A/F and control A/F after durability tests at near an excess air factor $\lambda=1$. The content of the noble metal in this layer is preferably not more than 2 mole % relative to the nonstoichiometric compound. If the content exceeds this value, emission gradually becomes at the rich side, and CO and the like become exhausted. By using such an element, the control A/F ratio of the sensor has little variations at the initial stage as well as after applications for a long period of time.

It has further been turned out, however, that, although the sensor element is more effective than conventional oxygen sensor elements when Si components are included within exhaust gases, it is shifted to the lean side to a large extent.

Accordingly, in the present invention (common through all the aspects), by including at least one silicon-reactive component selected from the group consisting of IIa subgroup elements in the international periodic table (termed hereinafter a "IIa subgroup component") in a silicon-reactive state and silicon-reactive components thereof within the protective layer (including that carrying a noble metal), Si components can be subjected to adsorption reaction by the protective layer before Si components within exhaust gases reach the active site (or region) of the sensor.

Presumably, it is due to the fact that since the IIa subgroup component, especially Ca and/or Mg, within the protective layer, reacts with Si components contained within exhaust gases at a temperature at which the sensor is used to produce crystals having a low melting point, Si components do not penetrate into an air-permeable protective layer (a first protective layer) which consists of a heat-resistant metal oxide. (especially of spinel and/or $Al_2O_3$) and does not contain a IIa subgroup component, and a noble metal and electrodes which exist within the first protective layer are therefore protected. As the IIa subgroup component, since especially chlorides and carbonates containing Ca or Mg (or the both) can form very fine particles, they can prevent the Si components from passing through, and also are highly active to the Si.

However, when Si contained within the exhaust gas is mixed at a low engine revolution, that is, at a low temperature, Si-adsorbing effect by the IIa subgroup component (especially Ca and Mg/or compounds) is weakened, and Si components occasionally penetrates into the protective layer without performing reaction. In such case, when the sensor is exposed at a high temperature, the Si is converted into $SiO_2$ and the like to occasionally produce clogging in the protective layer.

Accordingly, in a second aspect of the present invention, the penetration of the Si components at a low temperature can be prevented by providing a heater for heating the sensor element as well as including the IIa subgroup component within the protective layer on the side exposed to the exhaust gas. This is achieved due to the fact that by raising the temperature of the protective layer by the heater to increase the adsorption capability of the IIa subgroup component, the Si components can react with the IIa subgroup component to reduce the penetration of the Si alone.

In a third aspect of the present invention, as the base material for the protective layer (especially the carrier of the IIa subgroup component), its metal oxide is present as the nonstoichiometric compound. Si poisoning can thus more effectively be prevented. It is particularly preferred to combine those aspects described above.

As described above, according to the present invention, even if Si components exist in the exhaust gas, it is possible to prevent Si poisoning and to concentrate A/F ratio at near $\lambda=1$, and fall response property is also excellent. In addition, it is also possible to securely prevent deterioration in properties due to Si poisoning even at low engine revolutions or at low temperature of exhaust gas.

BRIEF DESCRIPTION OF THE DRAWINGS

FIG. 8(*a*) is its plan view (a protective layer is omitted), and FIG. 8(*b*) is its cross-sectional view;

FIG. 14 is a semi-cross-sectional view showing an oxygen sensor (a closed-tube-like oxygen sensor element) of the present invention;

FIGS. 15–17 are schematic drawings of enlarged cross-sections of II–IV in FIG. 14; FIG. 15 is that according to Example B-1, FIG. 16 is that according to Example B-2, and FIG. 17 is that according to Example B-3;

FIG. 18 is a schematic cross-sectional view showing an oxygen sensor according to Example B-4 which comprises a closed-tube-like element provided with a heater;

FIG. 19 is a plan view showing another oxygen sensor element (having the shape of a plate) of the present invention;

FIG. 20 is according to Example B-5, and FIG. 21 is according to Example B-6;

DESCRIPTION OF THE PREFERRED EMBODIMENTS

Figure 1:
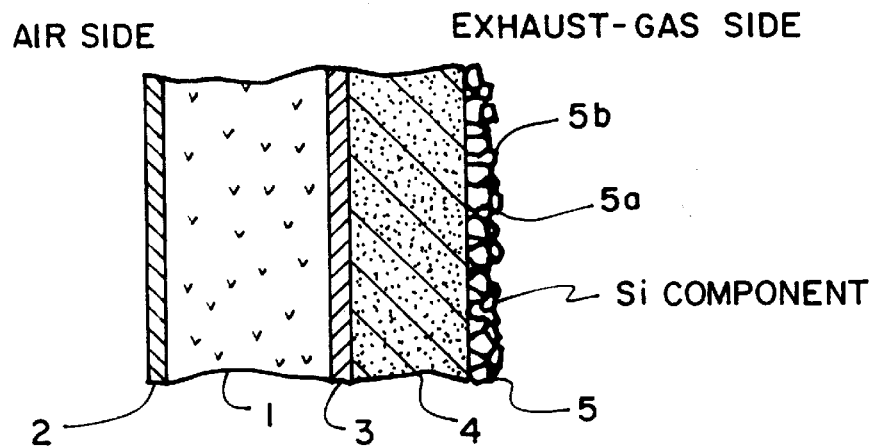
FIG. 1 is a partial cross-sectional view of a sensor schematically indicating the functions of the present invention.
Figure 2:
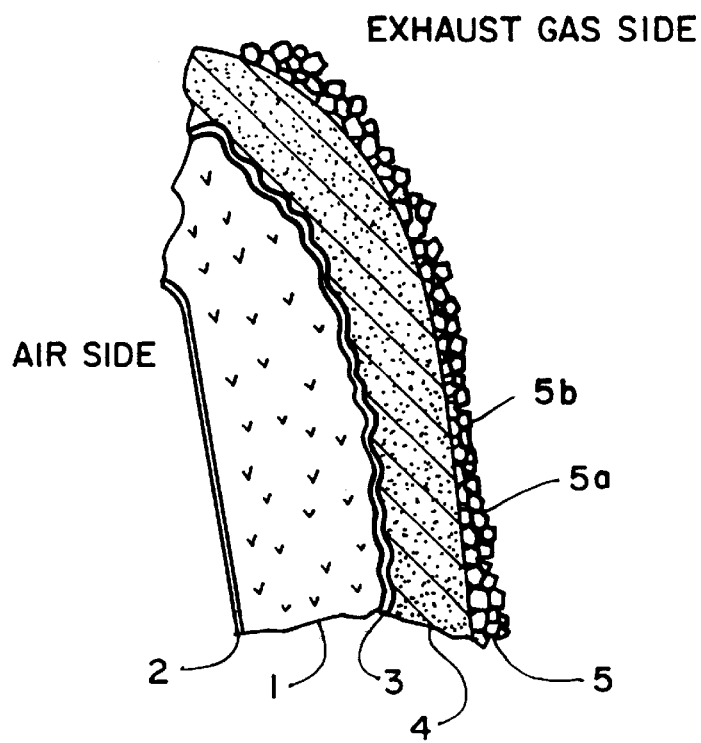
FIG. 2 is a partial cross-sectional view showing an embodiment of an oxygen sensor of the present invention.
Figure 3:
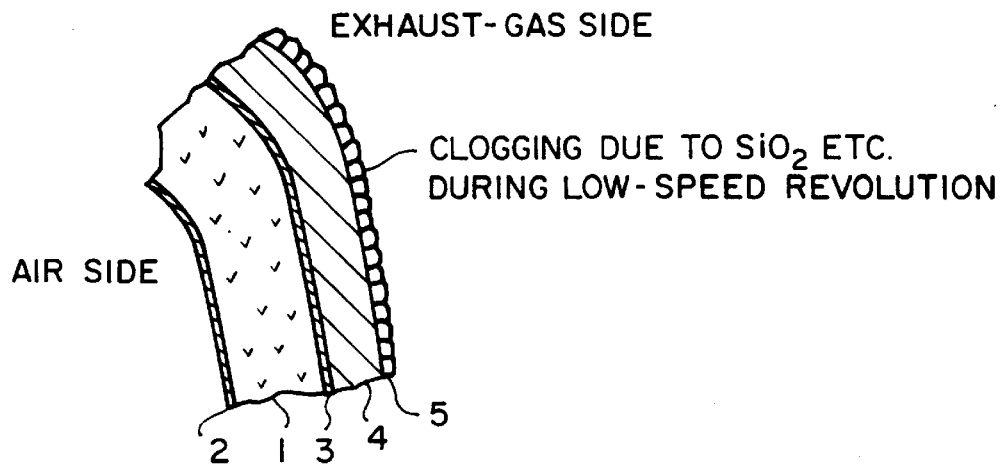
FIGS. 3 and 4 are partial cross-sectional views schematically indicating the functions of the present invention (FIG. 3 is a case where there is no heater, and FIG. 4 is a case where there is a heater)
Figure 4:
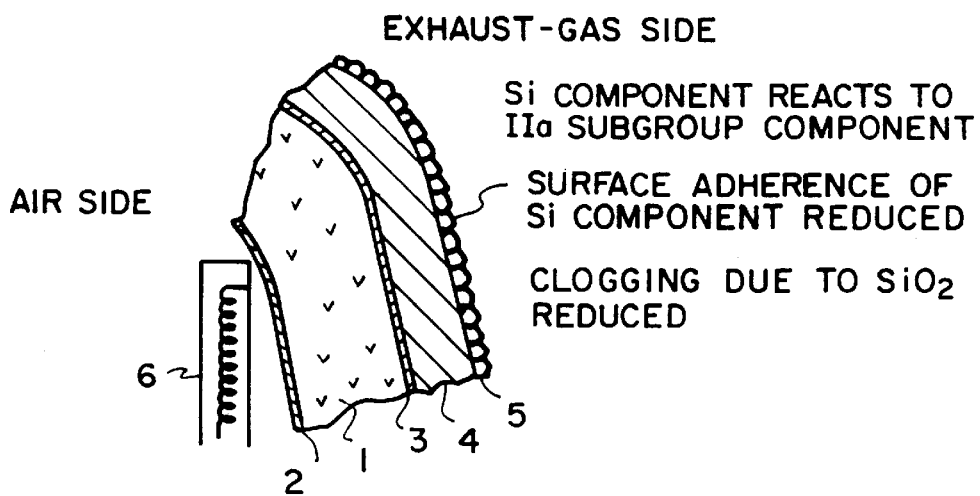
Figure 5:
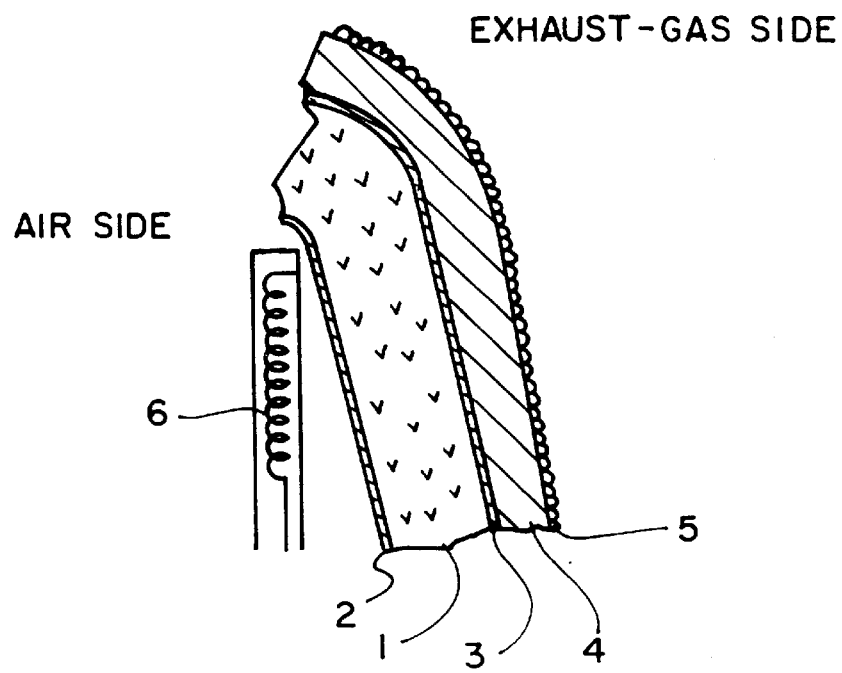
FIG. 5 is a partial cross-sectional view showing an embodiment of an oxygen sensor (having the shape of a closed tube) of the present invention.
Figure 6:
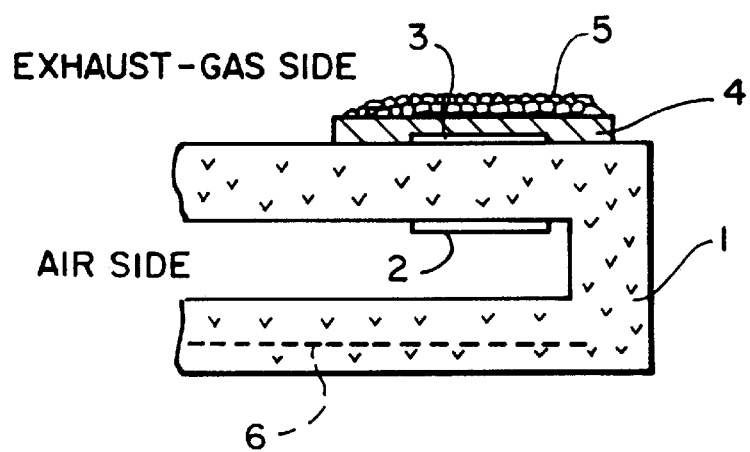
FIG. 6 is a partial cross-sectional view showing a further embodiment of an oxygen sensor (having the shape of a plate) of the present invention.

As for the protective layer (the second protective layer) containing the IIa subgroup component, Ca and/or Mg are excellent as the IIa subgroup elements. As for the composition of the IIa subgroup component, nonoxides, for example, chlorides, carbonates and nitrate salts, such as $CaCl_2$, $MgCO_3$ and the like, are preferred. In an oxygen sensor provided with a heater, however, even oxides are effective. Furthermore, their hydrates, for example, $CaCl_2 \cdot 2H_2O$, complex compounds such as $CaCO_3 \cdot MgCO_3$ (dolomite), may also be used. The Ea subgroup component may be carried on a heat-resistant metal oxide, such as $Al_2O_3$, titania and the like. It is especially preferred to be carried on a nonstoichiometric compound of the heat-resistant oxide, for example, $TiO_{2-x}$ and $La_2O_{3-x}$, with IIa subgroup component being highly dispersed in the carrier. The values of x's for $TiO_{2-x}$ and $La_2O_{3-x}$ are preferred to be $0<x\leq0.2$ and $0<x\leq0.3$, respectively.

As for its production method, there are a method in which the IIa subgroup component has previously been carried on, for example, titania particles (having an average particle size of, for example, 0.1–1 $\mu$m), the resultant particles are coated on the first protective layer as a slurry, and the coated layer is subjected to heat treatment (for example, 500°–700° C.), a method in which titania particles are coated on the first protective layer, the coated layer is then dipped in a solution of the IIa subgroup component under a reduced pressure or under a pressurized condition, and the resultant layer is subjected to heat treatment, and the like. In these cases, the ratio of the IIa subgroup component relative to the heat-resistant metal oxide of the second protective layer may be not more than 30 wt % based on the IIa subgroup element, and, more preferably, not more than 20 wt %. If the content exceeds 30 wt %, the responsive property of the sensor gradually becomes worse, that is, clogging starts to occur.

In order to prevent deterioration in durability of a noble metal as an electrode or a catalyst, it is necessary that at least a part of the heat-resistant metal oxide is present as a nonstoichiometric compound, for example, $TiO_{2-x}$. It is unnecessary, however, that the entire heat-resistant metal oxide is a nonstoichiometric compound, but the IIa subgroup component may also be dispersed and carried together with a stoichiometric compound (for example, $TiO_2$, $Al_2O_3$ and/or spinel). In this case, the existence ratio of a nonstoichiometric compound to a stoichiometric compound may be not less than 3:2, and, more preferably, not less than 2:1.

Furthermore, by including a noble metal, preferably Pt, in an amount of not more than 2 mole % (more preferably, not less than 0.2 mole %, and not more than 1.5 mole % under conditions of concentrated (rich) exhaust gases) relative to the nonstoichiometric compound, it is possible to further suppress variations in the initial control A/F ratio. In this case, as the second protective layer, a IIa subgroup component and a noble metal may be present in an identical portion, or the second protective layer may also consist of portions in which a noble metal is carried (a first protective portion) and a portion in which IIa subgroup component is carried (a second protective portion). In the latter case, however, it is necessary to dispose the second protective portion at a more outer side. Heat-resistant metal oxides for the first and second protective portions are preferably made of both nonstoichiometric compounds. As for the first protective portion, it is necessary that a nonstoichiometric compound exists in an amount of not less than 60%. It is also preferred that the IIa subgroup component is present independently of the heat-resistant metal oxides for the protective layer. The term "independently" or "independent" indicates that the IIa subgroup component does not react to the metal oxides to form compounds which are inert to Si components, such as $MgTiO_3$.

A protective layer (a first protective layer), which is disposed on a more inner side than the second protective layer and directly covers the electrode and which does not contain the IIa subgroup component, may also be provided. The first protective layer may be made of a heat-resistant metal oxide (spinel ($MgO \cdot Al_2O_3$) and/or alumina are particularly preferred, and may be firmly adhered to be coated by flame spraying. Inclusion of noble metals, for example, Pt, Rh and/or Pd within the first protective layer will result in complete oxidation and reduction of unburnt components in the exhaust gas and provision of control A/F ratio which is excellent for a sensor. A third protective layer made of, for example, titania, alumina, spinel and the like, may also be provided on the outer side of the second protective layer.

It is of course necessary that each protective layer has an air permeability to a degree such that does not deteriorate the response property of the sensor. For that purpose, the first protective layer may have plenty of fine pores with a porosity of roughly 10–30% and a thickness of roughly 10 to 50–150 $\mu$m. For the second protective layer, fine pores may have, for example, a porosity of 8–35% and a thickness of 10–50 $\mu$m.

The surface on the side of the measuring electrode of the main body of the sensor element made of, for example, zirconia solid electrolyte, may have a structure having a roughness in a depth of not less than 10 $\mu$m. This structure prevents peeling of the protective layer and is therefore excellent in durability.

As the material for the main body of the sensor element, $TiO_2$, CoO semiconductors and the like may also be used. As the nonstoichiometric compound, lanthanum oxide may also be used other than $TiO_{2-x}$, (Ti oxide). As for the heater, any kinds, materials (for example, ceramics) and mounting positions may be allowed as long as the above-described functions are provided.

EXAMPLES (A-1 to A-6)

Example A-1 (Table A1, Sample Nos. 1–14)

(1) Main bodies of the sensor element (provided with the electrodes and the first protective layer) were produced by the following steps 1–9.

Step 1:
5 mole % $Y_2O_3$ having a purity of 99% was added to $ZrO_2$ having a purity of not less than 99% and subjected to wet blending, and the resultant mixture was calcined at 1300° C. for 2 hours.

Step 2:
Adding water, the calcined material was pulverized in a ball mill in a wet state until 80% of the particles had particle sizes of not more than 2.5 $\mu$m.

Step 3:
A water-soluble binder was added, and spherical granulated particles having an average particle size of 70 $\mu$m were obtained by spray drying.

Step 4:
The granulated particles obtained at step 3 were formed into a desired tube-like shape (the shape of a U-tube) by rubber pressing and dried. The formed material was then ground into a predetermined shape by a grinding tool.

Step 5:
A sludge, which was made by adding a water-soluble binder, cellulose sodium glycolate and a solvent to the granulated particles obtained in step 3, was applied on the outer surface of the sample piece obtained in step 4.

Step 6:
After being dried, the sample piece obtained in step 5 was fired at 1500° C. for 2 hours. The portion corresponding to the detection portion had a length in axial direction of 25 mm, an outer diameter of about 5 mm$\phi$, and an inner diameter of about 3 mm$\phi$.

Step 7:
A Pt measuring electrode layer 0.9 $\mu$m thick was deposited on the outer surface of the resultant sample piece of step 6 by electroless plating, and then baked at 1000° C.

Step 8:
$MgO \cdot Al_2O_3$ (spinel) powder was plasma sprayed to form a first protective layer which directly covers the electrode about 100 $\mu$m thick.

Step 9:
A Pt reference electrode layer was formed on the inner surface of the resultant sample piece of step 8 in the same manner as step 7 resulting in a main body of the sensor element.

(2) The flame-sprayed portion of spinel of the main body of sensor element was dipped into $H_2PtCl_6$ solution containing 0.05 g/l Pt, and evacuated to cause a noble metal (Pt) to be carried within the first protective layer. The carried amount of Pt was about 0.02–0.05 wt % relative to the metal oxide of the first protective layer.

(3) The IIa subgroup component, such as $CaCl_2 \cdot 2H_2O$ (dissolved in pure water) and the like, were added to $TiO_{2-x}$ powder having an average particle size of about 0.2 $\mu$m, dried while boiling and stirring, and then the resultant mixture was subjected to heat treatment at 550° C. In Sample Nos. 11 and 12, $\alpha$-$Al_2O_3$ was also added. The $TiO_{2-x}$ powder was obtained by previously treating $TiO_2$ particles under nonoxidizing atmosphere at a temperature not less than 600° C. A nonstoichiometric compound may also be obtained by including a noble metal as much as 0.01 mole % relative to $TiO_2$. For carrying a noble metal on the titania powder, the titania particles were dipped into a solution of a salt containing a desired noble metal, boiled and dried, and then the resultant particles were subjected to heat treatment in air at 550° C.

(4) An organic binder and butyl carbitol were added to the powder obtained at process (3) and the resultant mixture was coated on the element obtained at process (2) by a brush and baked. The baking was performed under a reducing atmosphere at 500° C.

(5) A sensor assembly was performed in a known manner.

Example A-2 (Table A2, Sample Nos. A15–A27)

(1) and (2): Identical to processes (1) and (2) in the abovementioned Example A-1.

(3) An organic binder and butyl carbitol were added to $TiO_{2-x}$ powder having an average particle size of about 0.2 $\mu$m, and the resultant mixture was coated on the element obtained at process (2) by a brush and dried. The drying was performed in air at 120° C.

(4) $CaCl_2 \cdot 2H_2O$ was dissolved in water. The coated portion of the element obtained at process 3 was dipped in the solution and evacuated. At that time, Ca concentration was changed in various values. The samples were then dried in air at 100° C.

Example A-3 (Table A3, Sample Nos. 28–35)

(a) Production of the sensor element
Identical to that in Examples A-1 or A-2 described above.

(b) Production of the heater etc.
(1) A sheet comprised mainly of $Al_2O_3$ was formed into a thickness of 0.8 mm by the doctor blade method.

(2) Using a paste made by adding an organic binder and a solvent to W as the main component, a conductive pattern was printed by the screen printing method.

(3) Using a paste made by adding an organic binder and a solvent to $Al_2O_3$ as the main component, an additional coating 30 $\mu$m thick was further provided.

(4) The sheet obtained at process (3) was wound around an insulating tube having an outer diameter of 2 mm and comprised mainly of $Al_2O_3$, resin was removed at 400° C. for 24 hours, and the resultant tube was fired at 1550° C. for 2 hours.

(5) Lead wires were silver brazed at terminal portions to provide a heater.

(6) When assembling the element, the heater obtained at processes (1)–(5) was inserted so as not to contact the inner surface of the closed-tube-like element.

Example A-4 (Table A3, Sample Nos. A37–A39)

1. A sheet comprised mainly of $ZrO_2$+5 mole % $Y_2O_3$ was formed by the doctor blade method into a thickness of 0.8 mm.

(2) Using a paste made by adding an organic binder and a solvent to Pt as the main component, electrodes 20 $\mu$m thick were printed on both surfaces of the sheet by the screen printing method.

(3) A paste, which was made by adding an organic binder, a solvent and further a small amount of starch or the like for the purpose of providing a porous material to a main component $Al_2O_3$, was coated so as to coat the electrodes in a thickness of 30 $\mu$m.

(4) A paste, which was made by adding an organic binder and a solvent to $Al_2O_3$, was coated on two surfaces of a sheet identical to that in process 1 to a thickness of 30 $\mu$m.

(5) A heater pattern 20 $\mu$m thick was printed using a paste identical to that used in process (2).

(6) Process (4) was further repeated (on the surface of the heater pattern except the electrode).

(7) A sheet identical to that in process (1) was cut in the form generally of U, and the spacer sheet was interposed between the sheet printed with the electrode obtained at processes (1)–(3) and the sheet incorporating the heater pattern obtained in processes (4)–(6), and the entire lamination was subjected to thermocompression bonding.

(8) After resin was removed at 400° C. for 24 hours, the laminate was fired at 1500° C. for 4 hours.

(9) The protective layer carrying titania and the IIa subgroup component was formed. As for the second protective layer, Sample No. A37 is identical to Sample No. A3 in Example A-1, and Sample Nos. A38 and A39 are identical to Sample Nos. A17 and A18 in Example A-2, respectively.

Example A-5 (Table A4, Sample Nos. A40–A55, A60 and A61)

(1) Identical to that in process 1 (steps 1–9) in Example A-1 described above.

For Sample Nos. A45–A48, the noble metal was impregnated into the first protective layer in the same way as in process 2 in Example A-1 described above.

(2) $TiO_2$ powder (having an average particle size of 0.3 $\mu$m) was dipped in $H_2PtCl_6$ solution containing 0.05 g/l–1 g/l Pt and/or $RhCl_3 \cdot xH_2O$ solution containing 0.05 g/l Rh, and left under a reduced pressure of 50–100 mmHg for about 5 minutes to impregnate Pt or Rh so as to be contained in an amount corresponding to 1 mole % relative to $TiO_2$. The resultant powder was then dried, subjected to heat treatment in air at 600° C., and a paste was provided by further adding an organic binder and a solvent.

(3) The paste was coated on the first protective layer, and dried at 120° C. (the first protective layer portion 20 $\mu$m thick).

(4) Titania powder was dipped in a solution of, such as $CaCl_2 \cdot 2H_2O$ and the like, and the dried while boiling. A paste was then provided by adding a water-soluble binder and water. The amount of the IIa subgroup component was 20 wt % relative to $TiO_2$ based on the IIa subgroup metal.

(5) the paste was coated on the first protective layer, and baked at 600° C. (the second protective layer portion 20 $\mu$m thick).

(6) A third protective layer was properly formed on the second protective layer (consisting of the first and second protective portions). Furthermore, samples of various kinds of multilayer structure were prepared as shown in Table A4.

(7) The sensor assembly was performed in a known manner.

Example A-6 (Table A4, Sample Nos. A56–A59)

(1) Identical to that in processes (1)–(8) in Example A-4 described above. For Sample Nos. A58 and A59, however, a noble metal was included within the protective layer comprised of $Al_2O_3$ in the same way as in Example A-2.

(2) A paste identical to that used in process (3) in Example A-5 was coated, and baked in air at 600° C. to form the first protective portion (20 $\mu$m thick).

(3) A paste identical to that used in process (5) in Example A-5 was coated, and baked in air at 600° C. to form the second protective portion (20 $\mu$m thick).

(4) A pair of support members were mounted on both sides of the element thus obtained by glass seal.

(5) The sensor assembly was performed in a known manner.

Figure 7:
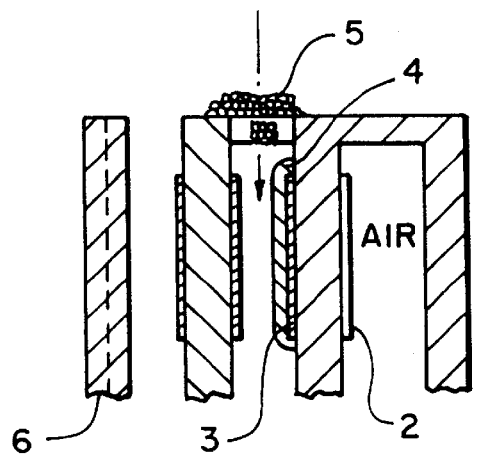
FIG. 7 is a cross-sectional view showing an oxygen sensor for full-range A/F ratio control (also provided with a pumping element) according to the present invention.
Figure 8A:
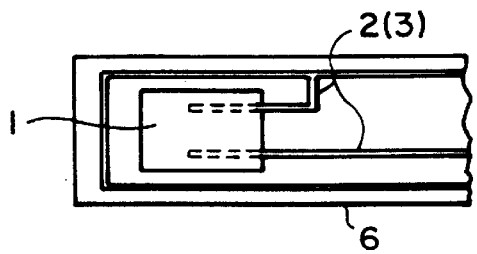
FIGS. 8(*a*) and 8(*b*) provide diagrams showing a semiconductor-type oxygen sensor according to the present invention.
Figure 8B:
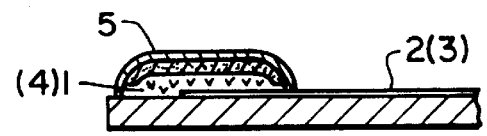
Figure 9:
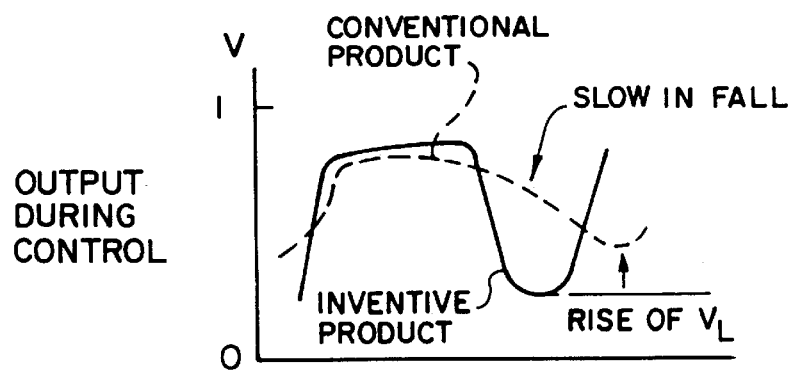
FIG. 9 is a schematic diagram of waveforms showing outputs during control after tests.

The present invention is not limited to the abovedescribed examples, but may also be applied to various types of oxygen sensors for A/F ratio control, for example, a full-range sensor for A/F ratio control also provided with a pump and the like (see FIG. 7), and to a sensor utilizing a metal-oxide semiconductor, such as $TiO_2$, CoO and the like (see FIG. 8). In the case with a semiconductor-type sensor, a noble metal may, for example, be included within a metal oxide which is a semiconductor, a flame-sprayed layer of spinel and the like may be provided, and a second protective layer containing a IIa subgroup component may be provided.

FIGS. 1–8 show oxygen sensors according the present invention. In these figures, there are shown a main body of a sensor element 1, a reference electrode 2, a measuring electrode 3, a first protective layer 4, a second protective layer 5, a heat-resistant metal oxide (particularly a nonstoichiometric compound) 5b, a IIa subgroup component 5a, and a heater 6.

Tests

The following tests were performed for each of the samples.

1. The initial control A/F of the sensor was measured in a real vehicle. As for the measuring method, the sensor was mounted to a manifold, and the engine was controlled by the sensor when the running condition was fixed at 80 km/hr×8 PS, and the A/F ratio in the exhaust gas was measured by an A/F-ratio meter.

2. The sensor was mounted to an exhaust pipe (about 1 m downstream from the manifold), and the engine was driven at 3000 rpm (1000 rpm when a heater was attached except Sample Nos. A28–A39) while further injecting silicone oil from the manifold portion at a rate of 5 cc/30 min for 1 hour (in total 10 cc)[Si test]. The atmosphere was at near an excess air factor $\lambda$=1.

Figure 10:
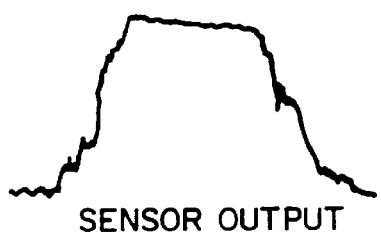
FIGS. 10 and 11 are diagram showing a waveform of a sensor output and defining measured times ($T_{LR}$ and $T_{R\,L}$), respectively.
Figure 11:
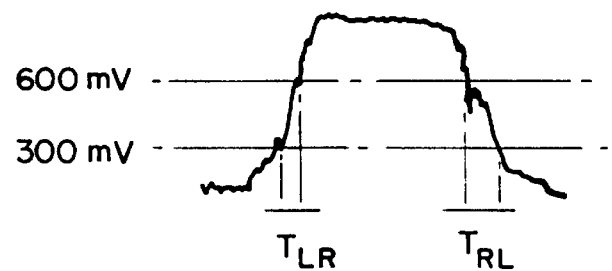

3. The measurement in test 1 was performed to obtain a change in A/F ($\Delta$A/F) between the initial stage and after the durability test. As the sensor's response property, the sensor output was monitored by a high-speed response recorder (see, for example, FIG. 10). As shown in FIG. 11, by drawing rectified gradient curves of the actually plotted curves with variations, time intervals between 300 mV and 600 mV ($T_{LR}$ and $T_{R\ L}$) were measured after the Si test.

4. For Sample Nos. A28–A39, a current was passed through the heater (except Sample No. A35) at the engine revolutions of 1000 rpm and 3000 rpm while injecting silicone oil, and the control state of the sensor was observed.

5. In the engine of a real vehicle a heat cycle test between 850° C. (30 minutes)←→ idling (30 minutes) was performed for 1000 hours at excess air factor λ=1, and the control A/F was measured.

Figure 12:
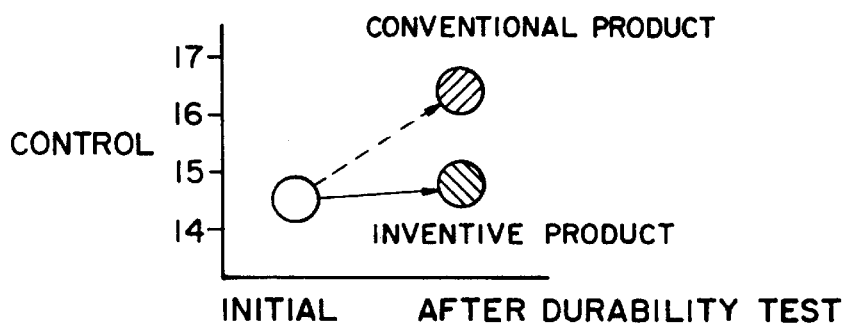
FIG. 12 is a graph showing the initial control A/F and changes in the control A/F after durability tests.
Figure 13:
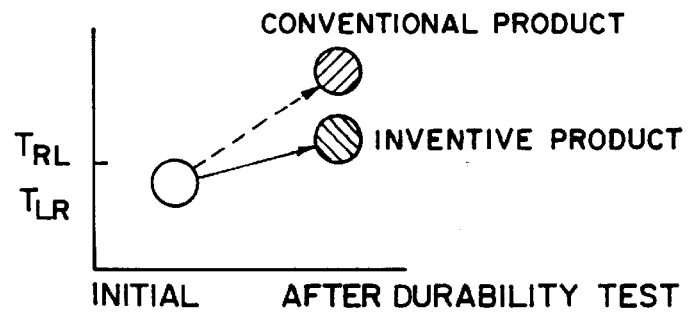
FIG. 13 is a graph showing the initial ($T_{LR}$ and $T_{R\,L}$) and changes in ($T_{LR}$ and $T_{R\,L}$) after durability tests.

The results of these tests are shown in Tables A1–A4 and FIGS. 12 and 13.

As is apparent on Tables A1–A4, in the comparative examples which are outside of the range of the present invention, variations in the A/F ratio are large ($\Delta A/F \geq 0.08$) and fall response property also becomes slow ($T_{R\ L} \geq 120$ msec) at Si tests. Furthermore, also in the heat cycle tests, variations in the A/F ratio are large ($\Delta A/F=0.04$).

On the other hand, in each of samples in the Examples, variations in the A/F ratio are significantly suppressed ($\Delta A/F \leq 0.04$), and the response property is also maintained at a high level ($T_{R\ L} \leq 90$ msec). Furthermore, in the heat cycle tests, variations in the A/F ratio are suppressed ($\Delta A/F \leq 0.02$).

From the results shown in Table A3, in the case of a low revolution (low temperature) of 1000 rpm and 300° C., $\Delta A/F$ becomes large when the heater does not exist (Sample No. A35). This is considered to be caused by the adsorption effect by the IIa subgroup component is weakened when Si is mixed at a low temperature. On the other hand, in each of the elements Nos. A28–A34 and Nos. A37–A39 in the Examples provided with the heater, variations in the A/F ratio can be significantly suppressed even after the Si tests at such a low temperature ($\Delta A/F \leq 0.05$).

It was also confirmed that, when the IIa subgroup component and the noble metal are provided in separate protective portions in the second protective layer, the initial A/F value has a tendency of rich control.

EXAMPLES (B-1 to B-7)

In FIGS. 14–26, there are shown an oxygen sensor A, an oxygen sensor element B, a pumping element C having a pair of electrodes, an oxygen-ion conductor 1, a reference electrode 2, a measuring electrode 3, a first protective layer 4, a second protective layer 5, a IIa subgroup component 5a, a heater 6, support members 7 of the element, a housing 8, a ring 9 for calking and a filler 10.

Example B-1

Oxygen sensors (Sample Nos. B1–B10) comprising closed-tube-like oxygen sensor elements having protective layers as shown in FIGS. 14 and 15 were obtained by the following steps.
(1) Production of the element
Step 1:
  5 mole % $Y_2O_3$ having a purity of 99% was added to $ZrO_2$ having a purity of not less than 99%, mixed, and the resultant mixture was calcined at 1300° C. for 2 hours.
Step 2:
  Adding water, the calcined material was pulverized in a ball mill in a wet state until 80% of the particles reached particle sizes of not more than 2.5 μm.
Step 3:
  A water-soluble binder was added, and spherical granulated particles having an average particle size of 70 μm were obtained by spray drying.
Step 4:
  The particles obtained at step 3 were formed into a desired tube-like shape (the shape of a test tube) by rubber pressing and dried. The formed material was then ground into a predetermined shape by a grinding tool.
Step 5:
  A sludge, which is made by adding a water-soluble binder, cellulose sodium glycolate and a solvent to the granulated particles obtained in step 3, was applied on the outer surface of the sample piece obtained in step 4.
Step 6:
  After being dried, the sample obtained in step 5 was fired at 1500° C. for 2 hours. The portion corresponding to the detection portion had a length in axial direction of 25 mm, an outer diameter of about 5 mmφ, and an inner diameter of about 3 mmφ.
Step 7:
  A Pt measuring electrode layer 0.9 μm thick was deposited on the outer surface of the resultant sample piece of step 6 by electroless plating, and then fired at 1000° C.
Step 8:
  $MgO \cdot Al_2O_3$ (spinel) powder was plasma sprayed to form an electrode protective layer (a first protective layer) about 150 μm thick. For Sample Nos. B5–B10, B15–B18 and B31–B34, a noble metal was contained in the spinel powder.
Step 9:
  A Pt reference electrode layer was formed on the inner surface in the same manner as step 7.
Step 10:
  At least the first protective layer was dipped into $H_2PtCl_6$ solution containing 0.05 g/l Pt, and left under a reduced pressure of 50–100 mmHg for about 5 minutes to impregnate a noble metal into the first protective layer.
Step 11:
  A chloride, carbonate or nitrate salt of a IIa subgroup element was coated on the first protective layer by an atomizer, and processed under a nonoxidizing atmosphere at a temperature not more than 600° C. to form a second protective layer (5–30 μm thick) resulting in a sensor element.
(2) Production of the oxygen sensor
  Using the oxygen sensor element B thus produced, the oxygen sensor A was obtained by the following steps as shown in FIG. 14.
Step 1:
  After inserting the element B into a housing 8, a ring 9 for calking and a filler 10, such as talc or carbon, were loaded to secure an element B within the housing 8.
Step 2:
  Leads were connected to electrodes 2 and 3 via terminals.
Step 3:
  A protective tube 11 was disposed covering the distal end portion of the element B, and the distal end of the housing 8 and the rear end of the protective tube 11 were welded together.
Step 4:
  An outer metal tube was covered to obtain an oxygen sensor.

Example B-2

In place of the production step 11 of the oxygen sensor element in Example B-1, the second protective layer was formed in the following manner. That is, water was added to a chloride, carbonate or nitric salt of a IIa subgroup element, $Al_2O_3$ powder having an average particle size of 0.5 82 m or $TiO_2$ powder having an average particle size of 0.3 μm was mixed, and the resultant mixture was coated on the first protective layer by an atomizer and processed under a nonoxydizing atmosphere at a temperature not more than 600° C. Otherwise in the same manner as Example B-1, oxygen sensors (Sample Nos. B11–B28) comprising the oxygen sensor elements of a closed tube-like shape and the protective layer(s) were obtained, as shown in FIGS. 14 and 16.

Example B-3

In place of step 11 of the oxygen sensor element in Example B-1, the second protective layer was formed in the following manner. That is, a chloride, nitric salt or the like of a IIa subgroup elements was dissolved in water, the first protective layer was dipped in the solution, left under a reduced pressure of 50–100 mmHg for about 5 minutes, and dried at 120° C. for 2 hours.

In the same manner as in Example B-1 for other steps, oxygen sensors (Sample Nos. B29–B34) comprising closed-tube-like oxygen sensor elements having protective layers as shown in FIGS. 14 and 17 were obtained.

Example B-4

Oxygen sensors (Sample Nos. B35–B41) having heaters as shown in FIG. 18 were obtained by the following steps.
(1) Production of the element
Identical to that in Examples B-1–B-3.
(2) Production of the heater and the like.
Step 1:
A sheet comprised mainly of $Al_2O_3$ was formed into a thickness of 0.8 mm by the doctor blade method.
Step 2:
Using a paste made by adding an organic binder and a solvent to W as the main component, a conductive pattern was printed by the screen printing method.
Step 3:
Using a paste made by adding an organic binder and a solvent to $Al_2O_3$ as the main component, a coating 30 μm thick was further provided.
Step 4:
The sheet obtained at step 3 was wound around an insulating tube having an outer diameter of 2 mm and comprised mainly of $Al_2O_3$, resin was removed at 400° C. for 24 hours, and the resultant tube was fired at 1550° C. for 2 hours.
Step 5:
Lead wires were silver brazed at terminal portions to provide a heater.
Step 6:
When assembling the element, the heater obtained at steps 1–5 was inserted so as not to contact the inner surface of the closed-tube-like element.

Example B-5

Figure 20:
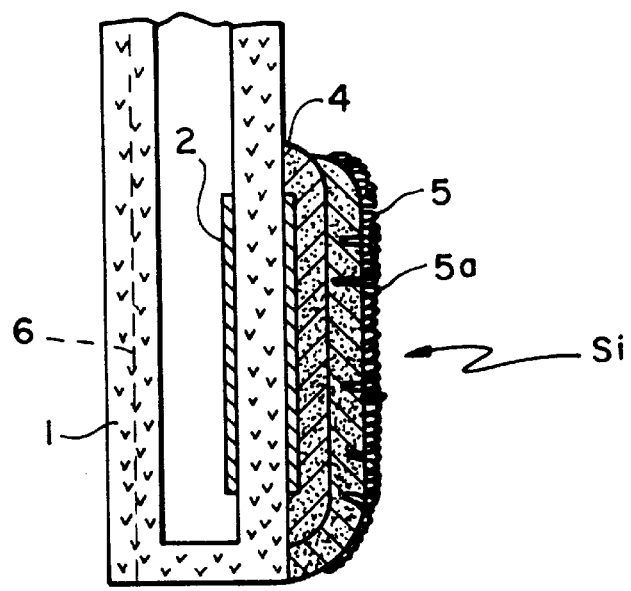
FIGS. 20 and 21 are schematic drawings of enlarged cross sections taken along lines VII and VIII in FIG. 19, respectively.

Oxygen sensors (Sample Nos. B42–B43) comprising a plate-like oxygen sensor element having protective layers as shown in FIGS. 19 and 20 were obtained by the following steps.
(1) Production of the element/heater
A sheet comprised mainly of $ZrO_2$ and containing 5 mole % $Y_2O_3$ was formed by a doctor blade method into a thickness of 0.8 mm.

Figure 22:
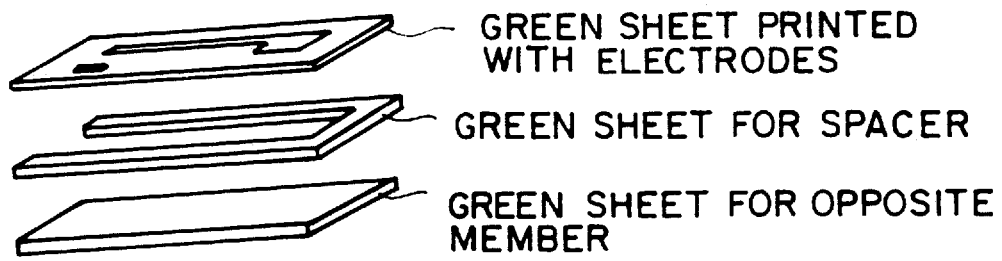
FIG. 22 is a diagram for explaining step 7 in Examples B-5 and B-6.
Figure 23:
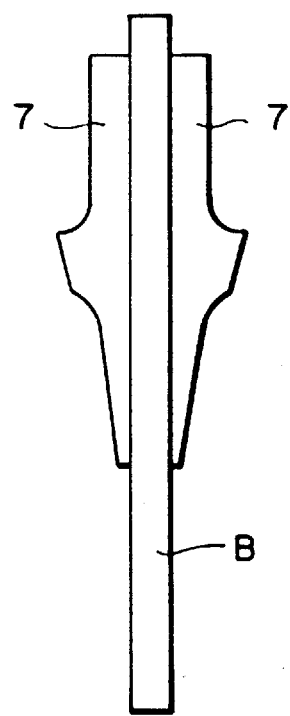
FIG. 23 is a diagram for explaining step 13 in Examples B-5 and B-6.

Step 2:
Using a paste made by adding an organic binder and a solvent to Pt as the main component, electrodes 20 μm thick were printed on both surfaces of the sheet by the screen printing method.
Step 3:
A paste, which was made by adding an organic binder, a solvent and further a small amount of starch or the like for the purpose of providing a porous material to $Al_2O_3$ as the main component, was coated so as to cover the electrodes to a thickness of 30 μm (formation of a porous $Al_2O_3$ layer as an electrode protective layer, i.e., a first protective layer).
Step 4:
A paste, which was made by adding an organic binder and a solvent to $Al_2O_3$ as the main component, was coated on two surfaces of a sheet having the same composition and thickness as those in step 1 to a thickness of 30 μm.
Step 5:
A heater pattern 20 μm thick was printed using the paste identical to that used in step 2.
Step 6:
$Al_2O_3$ was further coated in the same manner as step 4 (on the surface of the heater pattern except the electrode).
Step 7:
A sheet having the same composition and thickness as those in step 1 was cut in the form generally of U to provide a spacer sheet. As shown in FIG. 22, the spacer sheet was disposed between the green sheet printed with the electrode obtained in steps 1–3 and the green sheet for a facing member incorporating the heater pattern obtained in steps 4–6, and the entire laminate was subjected to thermocompression bonding.
Step 8:
After resin was removed at 400° C. for 24 hours, the laminate was fired at 1500° C. for 4 hours.
Step 9:
At least the porous $Al_2O_3$ layer (the first protective layer ) was dipped in an $H_2PtCl_6$ solution containing 0.05 g/l Pt, and left under a reduced pressure of 50–100 mmHg for about 5 minutes to impregnate the noble metal into the porous $Al_2O_3$ layer.
Step 10:
Using MgO·$Al_2O_3$ (spinel) powder, a spinel protective layer (a second protective layer) about 150 μm thick. was formed by flame spraying.
Step 11:
Water was added to chloride, carbonate, nitrate salt or the like of a IIa subgroup elements, the spinel protective layer was dipped in a solution thereof, left under a reduced pressure of 50–100 mmHg for about 5 minutes, and then dried at 120° C. for 2 hours. The layer was then subjected to heat treatment under a nonoxidizing atmosphere at 600° C.
Step 12:
As shown in FIG. 23, on the terminal side of the main body of the element thus obtained, a pair of support members 7 were mounted on both surfaces by glass seal.
(2) Production of the oxygen sensor
Identical to that in Example B-1.

Example B-6

In place of production steps 10 and 11 of the element/heater in Example B-5, the second protective layer was formed in the following manner. That is, water was added to a chloride, carbonate or nitric salt of a IIa subgroup elements, $Al_2O_3$ powder having an average particle size of 0.5 μm or $TiO_2$ powder having an average particle size of 0.3 μm was mixed, and the resultant mixture was coated on the porous $Al_2O_3$ layer (the first protective layer) by an atomizer and processed under a nonoxidizing atmosphere at a temperature not more than 600° C.

Figure 21:
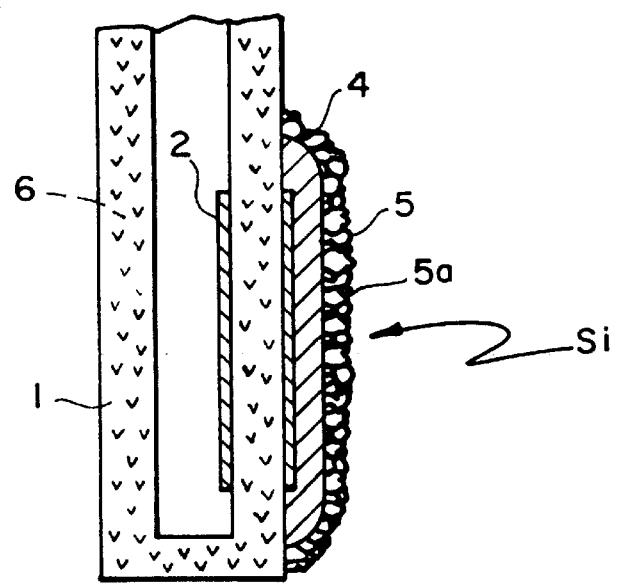

In the same manner as in Example B-5 for other steps, oxygen sensor (Sample Nos. B44–B46) comprising plate-like oxygen sensor elements having protective layers as shown in FIGS. 19 and 21 were obtained.

Example B-7

Figure 24:
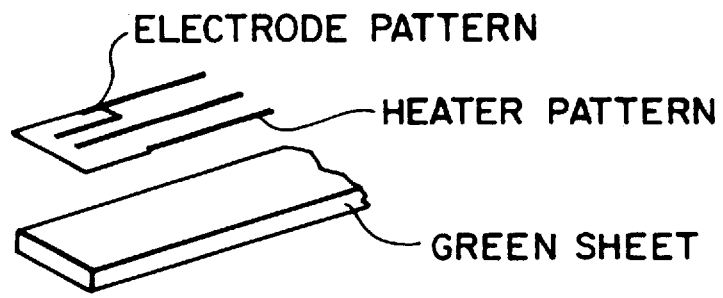
FIGS. 24 and 25 are diagrams showing steps 2 and 3 in Example B-7, respectively.
Figure 25:
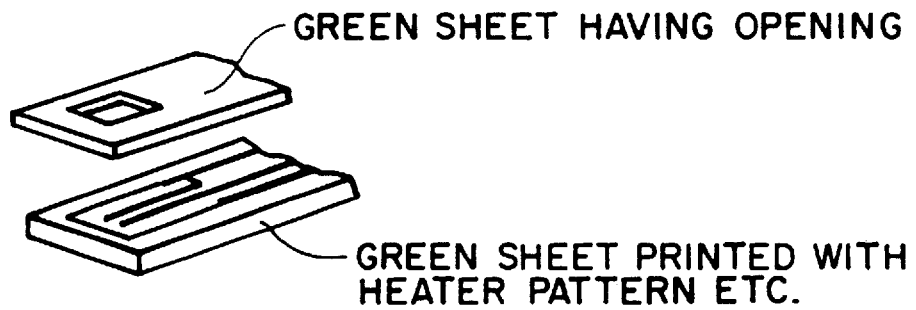
Figure 26:
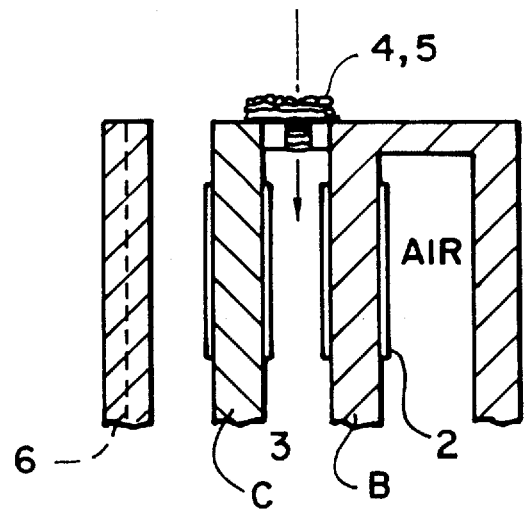
FIG. 26 is a cross-sectional view showing an A/F-ratio sensor as an embodiment of the present invention.

$TiO_2$ semiconductor-type oxygen sensors (Sample Nos. B47–B60) were obtained by the following steps.
(1) Production of the element
Step 1:

90 wt % $Al_2O_3$ having a purity of not less than 99% and 3, 2 and 5 wt % of MgO, CaO and $SiO_2$, respectively, were mixed, an organic binder and a solvent were added, and a green sheet 0.8 mm thick was provided by a doctor blade method.
Step 2:

Electrode and heater patterns (30 μm thick) shown in FIG. 24 were screen printed on a surface of the green sheet using a Pt paste.
Step 3:

A green sheet 250 μm thick was obtained in the same manner as in step 1, an opening was provided corresponding to the end portion of the electrodes, and the sheets were laminated as shown in FIG. 25.
Step 4:

After removing resin, the laminate was fired at 1500° C. for 2 hours.
Step 5:

$TiO_2$ having a purity of 99.9% was dipped in $H_2PtCl_6$ solution (it was arranged so that Pt became 1 mole % relative to $TiO_2$), and dried while boiling.
Step 6:

After being dried at 200° C. for 24 hours, the material obtained at step 5 was subjected to heat treatment under a nonoxidizing atmosphere at 1000° C. within a Pt crucible.
Step 7:

Pt black powder was added so as to be 5 mole % Pt relative to $TiO_2$, and an organic binder and a solvent were added to provide a paste.
Step 8:

The paste obtained at steps 5–7 was injected into the opening portion of the laminated body obtained at steps 1–4 to provide a layer 200 μm thick, which was subjected to heat treatment under a reducing atmosphere at 800° C.
Step 9:

After $Al_2O_3$ and MgO were laminated to a thickness of 50 μm by plasma spraying, the resultant laminate was dipped in a solution containing a IIa subgroup component to impregnate it under a pressure of 50–100 mmHg (sample Nos. B47 and B48).

Alternatively, a slurry made of a metal oxide comprised of $TiO_2$ or $Al_2O_3$ and a IIa subgroup component was coated (30 μm thick)(Sample Nos. B49 and B50).
(2) Production of the oxygen sensor
Identical to that in Example B-1.

Tests

The following tests were performed on Examples B-1–B-7.
(1) The initial control A/F of the sensor was measured in a real vehicle. As for the measuring method, the sensor was mounted to a manifold, and the engine was controlled by the sensor when the running condition was fixed at 80 km/hr ×8 ps, and the A/F ratio in the exhaust gas was measured by an A/F-ratio meter.
(2) The sensor was mounted to an exhaust pipe (about 1 m downstream from the manifold), and the engine was driven at 3000 rpm while further injecting silicone oil from the manifold portion at a rate of 5 cc/30 min for 1 hour (in total 10 cc). The atmosphere was nearly at an excess air factor λ=1. The engine was driven at 3000 rpm and 1000 rpm for testing on Nos. B35–B41 and comparative Examples BV and BVI, respectively.
(3) The measurement in test 1 was performed to obtain a change in A/F (ΔA/F) between the initial stage and after the durability test. As the sensor's response property, the sensor output was monitored by a high-speed response recorder (see, for example, FIG. 10). As shown in FIG. 11, by drawing rectified gradient curves of the actually plotted curves, time intervals between 300 mV and 600 mV ($T_{LR}$ and $T_{RL}$) were measured.
(4) The control state of sensors having heaters was observed in the same manner. Heaters were set at a temperature not less than 400° C.

The results are shown in Tables B1–B5.

It should be noted that modification may be done based on the concept and gist herein disclosed without departing from the scope hereinbelow claimed.

TABLE A[1)]

| | First protective layer | | Second protective layer | | | | | | | After SI test | | A/F ratio |
|---|---|---|---|---|---|---|---|---|---|---|---|---|
| | | | Oxide | | IIa subgroup Component | | Noble metal | | Initial | | | |
| Sample No. | Metal oxide | Noble metal | Component | Ratio (wt %) | Component | Ratio[2)] (wt %) | Component | Ratio[3)] (mole %) | A/F ratio | ΔA/F | $T_{LR}$ $T_{RL}$ (mS) | after heat cycle test |
| A1 | Spinel | $H_2PtCl_8$ | $TiO_2$ | 100 | $CaCO_3$ | 5 | — | — | 14.62 | 0.01 | 40 50 | 14.63 |
| A2 | ↑ | ↑ | ↑ | 100 | $CaCl_2.2H_2O$ | 5 | — | — | 14.62 | 0.01 | 40 50 | 14.63 |
| A3 | ↑ | ↑ | ↑ | 100 | ↑ | 5 | $H_2PtCl_6$ | 0.7 | 14.60 | 0.01 | 40 40 | 14.61 |
| * A4 | ↑ | ↑ | $Al_2O_3$ | 100 | ↑ | 5 | ↑ | 0.7 | 14.61 | 0.03 | 50 40 | 14.65 |
| A5 | ↑ | ↑ | $TiO_2$ | 100 | ↑ | 10 | — | — | 14.62 | 0.01 | 50 50 | 14.63 |
| A6 | ↑ | ↑ | ↑ | 100 | ↑ | 20 | — | — | 14.62 | ≦0.01 | 60 50 | 14.62 |
| A7 | ↑ | ↑ | ↑ | 100 | ↑ | 30 | — | — | 14.61 | ≦0.01 | 70 60 | 14.63 |
| A8 | ↑ | ↑ | ↑ | 100 | $MgCO_3$ | 5 | — | — | 14.62 | 0.02 | 40 50 | 14.63 |
| A9 | ↑ | ↑ | ↑ | 100 | Dolomite | 5 | — | — | 14.62 | ≦0.01 | 40 50 | 14.63 |
| A10 | ↑ | ↑ | ↑ | 100 | ↑ | 5 | $H_2PtCl_6$ | 0.7 | 14.60 | 0.02 | 40 40 | 14.62 |
| A11 | ↑ | ↑ | $TiO_2$ $Al_2O_3$ | 20 60 | $CaCl_2.2H_2O$ | 20 | — | — | 14.62 | 0.03 | 40 40 | 14.65 |

TABLE A[1])-continued

| | First protective layer | | Second protective layer | | | | | | Initial | After SI test | | A/F ratio |
|---|---|---|---|---|---|---|---|---|---|---|---|---|
| | | | Oxide | | IIa subgroup Component | | Noble metal | | | | | |
| Sample No. | Metal oxide | Noble metal | Component | Ratio (wt %) | Component | Ratio[2]) (wt %) | Component | Ratio[3]) (mole %) | A/F ratio | ΔA/F | $T_{LR}$ $T_{RL}$ (mS) | after heat cycle test |
| A12 | ↑ | ↑ | ↑ | 60 20 | ↑ | 20 | — | — | 14.62 | 0.01 | 40  50 | 14.63 |
| *A13 | ↑ | — | — | — | — | — | — | — | 14.64 | 0.12 | 150  240 | 14.64 |
| *A14 | ↑ | $H_2PtCl_6$ | $TiO_2$ | 100 | — | — | $H_2PtCl_6$ | 0.7 | 14.60 | 0.08 | 70  160 | 14.62 |

*Outside of the Inventive scope
[1])All the components in the table are shown by the compositions of starting materials.
"Spinel " is $MgO.Al_2O_3$ and
"$Al_2O_3$ is $\alpha$-$Al_2O_3$ (the same applies to the following tables).
[2])The ratio of the IIa subgroup component is relative to the metal oxide of the second protective layer (titania and $Al_2O_3$), and is a converted value into the IIa subgroup element (Ca, Mg) (the same applies to the following tables). Sample Nos. A11 and A12 are relative to the entire second protective layer (this applies to tho ratio of the metal oxide).
[3])The ratio of the noble metal is relative to the metal oxide (titania, $Al_2O_3$) of each protective layer.
Sample No. A4: ΔA/P was sowewhat large at heat cycle test and a part of the second protective layer peeled off. The first protective layer was also easily peeled off.
No. A7: Response was sowewhat slow from the initial stage, and there was tendency of clogging.
No. A11: ΔA/P was sowewhat large at heat cycle test.

TABLE A2

| | First protective layer | | Second protective layer | | | |
|---|---|---|---|---|---|---|
| | | | Oxide | | Noble metal | |
| Sample No. | Metal oxide | Noble metal | Component | Thickness (μm) | Component | Ratio[2]) (wt %) |
| A15 | Spinel | $H_2PtCl_6$ | $TiO_2$ | 10 | $H_2PtCl_6$ | 1 |
| A16 | ↑ | ↑ | ↑ | 10 | ↑ | 0.5 |
| A17 | ↑ | ↑ | ↑ | 20 | ↑ | 1 |
| A18 | ↑ | ↑ | ↑ | 20 | ↑ | 0.5 |
| A19 | ↑ | ↑ | ↑ | 20 | ↑ | 1 |
| A20 | ↑ | ↑ | ↑ | 30 | ↑ | 1 |
| A21 | ↑ | ↑ | ↑ | 30 | ↑ | 0.5 |
| *A22 | ↑ | ↑ | ↑ | 20 | ↑ | 1 |
| A23 | ↑ | ↑ | ↑ | 10 | ↑ | 1 |
| A24 | ↑ | ↑ | ↑ | 20 | ↑ | 0.5 |
| A25 | ↑ | ↑ | ↑ | 30 | ↑ | 1 |
| A26 | ↑ | ↑ | ↑ | 20 | ↑ | 0 |
| A27 | ↑ | ↑ | ↑ | 20 | ↑ | 0 |

| | Second protective layer | | | Initial | After Si test | | A/F ratio |
|---|---|---|---|---|---|---|---|
| | IIa subgroup | | | | | | |
| Sample No. | Component | Concentration[1]) (g/cc) | Ratio[3]) (wt %) | A/F ratio | ΔA/F | $T_{LR}$ $T_{4RL}$ (mS) | after heat cycle test |
| A15 | $CaCl_2.2H_2O$ | 3/100 | 5 | 14.62 | 0.04 | 60  80 | 14.63 |
| A16 | ↑ | 10/100 | 11 | 14.62 | 0.02 | 40  50 | 14.62 |
| A17 | ↑ | 3/100 | 3 | 14.60 | 0.03 | 50  50 | 14.62 |
| A18 | ↑ | 10/100 | 6 | 14.61 | 0.01 | 40  50 | 14.62 |
| A19 | ↑ | 20/100 | 14 | 14.63 | 0.02 | 70  70 | 14.02 |
| A20 | ↑ | 3/100 | 2 | 14.60 | 0.02 | 40  50 | 14.62 |
| A21 | ↑ | 10/100 | 4 | 14.62 | 0.01 | 40  40 | 14.63 |
| *A22 | — | — | — | 14.60 | 0.08 | 80  170 | 14.62 |
| A23 | $CaCl_2.2H_2O$ | 10/100 | 11 | 14.63 | 0.02 | 40  50 | 14.63 |
| A24 | ↑ | 10/100 | 6 | 14.62 | 0.01 | 40  40 | 14.63 |
| A25 | ↑ | 10/100 | 4 | 14.62 | 0.01 | 40  50 | 14.63 |
| A26 | ↑ | 3/100 | 3 | 14.63 | 0.03 | 50  60 | 14.64 |
| A27 | ↑ | 10/100 | 6 | 14.64 | 0.02 | 50  60 | 14.64 |

*Outside of the Inventive scope
[1])Ca concentration in aqueous solution of $CaCl_2$
[2])Based on amount of Pt.
[3])Based amount of Ca.
Sample No. A15: There was tendency of being sowewhat poisoned at Si test.
Sample No. A19: Response was sowewhat slow from the initial stage, and there was tendency of being clogged.

TABLE A3

| Sample No. | Element | Existence of heater | ΔA/F 3000 rpm[1] | ΔA/F 1000 rpm[1] |
|---|---|---|---|---|
| A28 | No. A3 | Yes | 0.02 | 0.03 |
| A29 | A6 | Yes | 0.01 | 0.02 |
| A30 | A12 | Yes | 0.01 | 0.02 |
| A31 | A15 | Yes | 0.03 | 0.05 |
| A32 | A17 | Yes | 0.02 | 0.04 |
| A33 | A18 | Yes | 0.01 | 0.02 |
| A34 | A27 | Yes | 0.02 | 0.03 |
| A35 | A17 | No | 0.03 | 0.09 |
| *A36 | A22 | Yes | 0.09 | 0.13 |
| A37 | (No. A3)[2] | Yes | 0.02 | 0.03 |
| A38 | (No. A17)[2] | Yes | 0.01 | 0.02 |
| A39 | (No. A18)[2] | Yes | 0.01 | 0.02 |

* Outside of the inventive range (Sample No. A35 is outside of claims defining heater).

[1] The sensor temperatures are about 400° C. (No current through the heater) and about 550° C. (current fed through the heater) at engine revolution of 3000 rpm. The sensor temperatures are about 300° C. (No current through the heater) and about 400° C. (current fed through the heater) at engine revolution of 1000 rpm.

[2] For Sample Nos. A37–A39, the main body and first protective layer of the element were formed by procsses (1)–(8) in Example A-4, then the second protective layers identical to those of element numbers shown within parentheses in the table were formed.

TABLE A4

| Sample No.[1] | First protective layer | | Second protective layer | | | | | | | Third protective layer | | Initial | After Si test | | | A/F ratio after heat cycle test |
|---|---|---|---|---|---|---|---|---|---|---|---|---|---|---|---|---|
| | Metal oxide | Noble metal | Metal oxide | Noble metal (IIa subgroup component) Component | Ratio[3] (mole %) | Metal oxide | IIa subgroup component (Noble metal) Component | Ratio[4] (wt %) | | Metal oxide | Noble metal | A/F ratio | ΔA/F | $T_{LR}$ (wS) | $T_{RL}$ (wS) | |
| A40 | Spinel | — | TiO$_2$ | H$_2$PtCl$_6$ | 1 | TiO$_2$ | CaCl$_2$.2H$_2$O | 20 | | — | — | 14.59 | 14.62 | 50 | 60 | 14.60 |
| A41 | ↑ | — | ↑ | ↑ | 1 | ↑ | CaCO$_3$ | 20 | | — | — | 14.58 | 14.64 | 60 | 70 | 14.60 |
| A42 | ↑ | — | ↑ | ↑ | 1 | Al$_2$O$_3$ | CaCl$_2$.2H$_2$O | 20 | | — | — | 14.60 | 14.64 | 60 | 70 | 14.61 |
| A43 | ↑ | — | ↑ | ↑ | 1 | TiO$_2$ | MgCO$_3$ | 20 | | — | — | 14.59 | 14.62 | 50 | 60 | 14.60 |
| A44 | ↑ | — | ↑ | RhCl$_3$.xH$_2$O | 1 | ↑ | CaCl$_2$.2H$_2$O | 20 | | — | — | 14.62 | 14.65 | 60 | 70 | 14.62 |
| A45 | ↑ | H$_2$PtCl$_6$ | ↑ | ↑ | 1 | ↑ | ↑ | 20 | | — | — | 14.61 | 14.65 | 60 | 80 | 14.61 |
| A46 | ↑ | ↑ | ↑ | ↑ | 1 | ↑ | MgCO$_3$ | 20 | | — | — | 14.58 | 14.62 | 50 | 60 | 14.60 |
| A47 | ↑ | ↑ | ↑ | H$_2$PtCl$_6$ | 1 | ↑ | ↑ | 20 | | — | — | 14.58 | 14.62 | 50 | 60 | 14.60 |
| *A48 | ↑ | ↑ | ↑ | ↑ | 1 | ↑ | ↑ | — | | — | — | 14.58 | 14.70 | 80 | 190 | 14.60 |
| *A49 | ↑ | — | ↑ | CaCl$_2$.2H$_2$O | 20 wt % | ↑ | H$_2$PtCl$_6$ | 1 mole % | | — | — | 14.58 | 14.67 | 80 | 150 | 14.62 |
| A50 | ↑ | — | ↑ | H$_2$PtCl$_6$ | 1 | ↑ | | | | | | | | | | |
| A51 | ↑ | — | ↑ | ↑ | 1 | ↑ | | | | | | | | | | |
| A52 | ↑ | — | ↑ | RhCl$_3$.xH$_2$O | 1 | ↑ | | | | | | | | | | |
| A53 | ↑ | — | ↑ | ↑ | 1 | ↑ | | | | | | | | | | |
| *A54 | ↑ | — | ↑ | — | — | ↑ | | | | | | | | | | |
| *A55 | ↑ | — | ↑ | — | — | ↑ | | | | | | | | | | |
| A56 | Al$_2$O$_3$ | — | ↑ | H$_2$PtCl$_6$ | 1 | ↑ | | | | | | | | | | |
| A57 | ↑ | — | ↑ | ↑ | 1 | ↑ | | | | | | | | | | |
| A58 | ↑ | H$_2$PtCl$_6$ | ↑ | RhCl$_3$.xH$_2$O | 1 | ↑ | | | | | | | | | | |
| *A59 | ↑ | ↑ | ↑ | ↑ | 1 | ↑ | | | | | | | | | | |
| *A60 | Spinel | — | ↑ | — | — | — | | | | | | | | | | |
| *A61 | ↑↑ | — | ↑ | H$_2$PtCl$_6$ | 1 | — | | | | | | | | | | |

TABLE A4-continued

| | | | | | | | | | |
|---|---|---|---|---|---|---|---|---|---|
| A50 | MgCO$_3$ | 20 | TiO$_2$ | — | 14.57 | 14.60 | 60 | 60 | 14.58 |
| A51 | ↑ | 20 | Al$_2$O$_3$ | — | 14.58 | 14.61 | 60 | 70 | 14.60 |
| A52 | ↑ | 20 | Spinel | — | 14.58 | 14.60 | 70 | 60 | 14.59 |
| A53 | CaCl$_2$.2H$_2$O | 20 | TiO$_2$ | — | 14.58 | 14.60 | 70 | 60 | 14.59 |
| *A54 | ↑ | 20 | ↑ | H$_2$PtCl$_2$ [2] | 14.58 | 14.66 | 60 | 120 | 14.62 |
| *A55 | RhCl$_3$.xH$_2$O | 1 mole % | ↑ | — | 14.58 | 14.69 | 70 | 170 | 14.62 |
| A56 | CaCl$_2$.2H$_2$O | 20 | — | — | 14.57 | 14.63 | 70 | 90 | 14.58 |
| A57 | MgCO$_3$ | 20 | — | — | 14.57 | 14.63 | 70 | 90 | 14.59 |
| A58 | ↑ | 20 | — | — | 14.56 | 14.62 | 70 | 80 | 14.58 |
| *A59 | — | — | — | — | 14.56 | 14.71 | 70 | 130 | 14.58 |
| *A60 | — | — | — | — | 14.64 | 14.72 | 90 | 230 | 14.62 |
| *A61 | — | — | — | — | 14.58 | 14.71 | 90 | 230 | 14.62 |

*Outside of the Inventive range.
[1] Each sample is provided with a heater except Sample Nos. A44 and A45.
[2] 1 mole %.
[3] Amount of noble metal.
[4] Amount of IIa subgroup element.

TABLE B1

| Sample No. | First protective layer Metal oxide | First protective layer Noble metal | Second protective layer (IIa subgroup component) | A/F ratio difference between the initial stage and after durability test | Response property after test (msec) Rise | Response property after test (msec) Fall |
|---|---|---|---|---|---|---|
| B1 | Spinel | — | CaCO$_3$ | 0.02 | 30 | 50 |
| B2 | ↑ | — | CaCl$_2$.2H$_2$O | 0.03 | 30 | 60 |
| B3 | ↑ | — | MgCO$_3$ | 0.04 | 40 | 70 |
| B4 | ↑ | — | CaCO$_3$.MgCO$_3$ | 0.02 | 30 | 60 |
| B5 | ↑ | Pt* 3% | CaCl$_2$.2H$_2$O | 0.02 | 40 | 60 |
| B6 | ↑ | Rh** 5% | ↑ | 0.02 | 40 | 70 |
| B7 | ↑ | Rh 1% | Ca(NO$_3$)$_2$ | 0.02 | 30 | 50 |
| B8[1] | ↑ | Rh 7% | ↑ | 0.03 | 50 | 60 |
| B9 | ↑ | Pt 3% | CaO | 0.09 | 90 | 160 |
| B10 | ↑ | Pt 3% | CaCl$_2$ | 0.03 | 30 | 60 |
| * BI | — | — | CaCl$_2$ baking | 0.03 [2] | 30 | 50 |
| * BII | Spinel | — | — | 0.12 | 150 | 230 |

* in H$_2$PtCl$_3$
** in RhCl$_3$.xH$_2$O
[1] Sample No. B8 produced cracks in the first protective layer at other durability tests (cycledurability test between 200° C. or below and 900° C. or above).
[2] A part of CaCl$_2$ peeled off.
When Al$_2$O$_3$ is used as the metal oxide of the first protective layer by the same production process as in Example B-1, there arises a problem in heat cycle durability tests due to a difference in thermal expansion from ZrO$_2$ oxygen-ion conductor.

TABLE B2

| Sample No. | First protective layer Metal oxide | First protective layer Noble metal | Second protective layer Metal oxide | Second protective layer IIa subgroup component [1] Composition | Second protective layer IIa subgroup component [1] Amount (wt %) | Initial control (Hz) | Differenace A/F ratio between initial stage and after durability test | Response property after test (msec) Rise | Response property after test (msec) Fall |
|---|---|---|---|---|---|---|---|---|---|
| B11 | Spinel[3] | — | Al$_2$O$_3$ | CaCO$_3$ | 15 | 2.12 | 0.02 | 30 | 60 |
| B12 | ↑ | — | ↑ | CaCl$_2$.2H$_2$O | ↑ | 2.05 | 0.02 | 30 | 50 |
| B13 | ↑ | — | ↑ | MgCO$_3$ | ↑ | 2.17 | 0.02 | 30 | 50 |
| B14 | ↑ | — | ↑ | CaCO$_3$.MgCO$_3$ | | 2.20 | 0.02 | 30 | 60 |
| B15 | ↑ | Pt 3% | ↑ | CaCl$_2$.2H$_2$O | ↑ | 2.17 | 0.03 | 40 | 60 |
| B16 | ↑ | Rh 5% | ↑ | ↑ | ↑ | 2.13 | 0.03 | 40 | 70 |
| B17 | ↑ | Rh 1% | ↑ | Ca(NO$_3$)$_2$ | ↑ | 2.10 | 0.03 | 40 | 60 |
| B18 [2] | ↑ | Rh 7% | ↑ | ↑ | ↑ | 2.03 | 0.03 | 50 | 70 |
| B19 | ↑ | Pt 3% | ↑ | CaO | ↑ | 2.19 | 0.08 | 80 | 140 |
| B20 | ↑ | Pt 3% | ↑ | CaCl$_2$.2H$_2$O | ↑ | 2.15 | 0.03 | 40 | 60 |
| B21 | ↑ | Pt 1% | ↑ | ↑ | 30 | 2.01 | 0.02 | 60 | 80 |
| B22 | ↑ | ↑ | ↑ | ↑ | 50 | 1.83 | 0.01 | 90 | 100 |
| B23 | ↑ | ↑ | TiO$_2$ | MgCO$_3$ | 20 | 2.16 | 0.02 | 50 | 70 |
| B24 | ↑ | ↑ | ↑ | ↑ | 40 | 1.91 | 0.01 | 70 | 80 |
| B25 | ↑ | ↑ | ↑ | MgO | 15 | 2.13 | 0.08 | 100 | 180 |

TABLE B2-continued

| | First protective layer | | Second protective layer | | | Difference A/F ratio between initial stage and after durability test | Response property after test (msec) | |
|---|---|---|---|---|---|---|---|---|
| | | | | IIa subgroup component [1] | | Initial control (Hz) | | |
| Sample No. | Metal oxide | Noble metal | Metal oxide | Composition | Amount (wt %) | | Rise | Fall |
| B26 | ↑ | ↑ | ↑ | CaCl$_2$.2H$_2$O | 2 | 2.22 | 0.07 | 80 | 70 |
| B27 | ↑ | ↑ | ↑ | ↑ | 10 | 2.18 | 0.02 | 40 | 60 |
| B28 | ↑ | ↑ | Spinel[3] | ↑ | 10 | 2.25 | 0.03 | 50 | 70 |
| Comparison BIII | ↑ | ↑ | Al$_2$O$_3$ | — | — | 2.26 | 0.12 | 150 | 230 |
| B29 | ↑ | — | — | CaCl$_2$.2H$_2$O | 0.5 | 2.23 | 0.07 | 70 | 90 |
| B30 | ↑ | — | — | ↑ | 10 | 2.06 | 0.04 | 50 | 80 |
| B31 | ↑ | — | — | ↑ | 20 | 1.73 | 0.02 | 50 | 70 |
| B32 | ↑ | Pt 1% | — | Mg(NO$_3$)$_2$ | 0.2 | 2.19 | 0.09 | 80 | 100 |
| B33 | ↑ | ↑ | — | ↑ | 5 | 2.12 | 0.05 | 60 | 70 |
| B34 | ↑ | ↑ | — | ↑ | 15 | 1.94 | 0.04 | 70 | 90 |
| Comparison BIV | ↑ | ↑ | — | — | — | 2.27 | 0.15 | 170 | 260 |

[1] The amount of the IIa subgroup component is the amount relative to the metal oxide (Al$_2$O$_3$, TiO$_2$) of the second protective layer and converted into the IIa Subgroup element (Ca, Mg); For Samaple Nos. B29–B34, the amount is relativeto the first protective layer.
[2] Sample No. B18 produced cracs ln the first protective layer at other engine durability tests (cycle durabillty test between not more than 200° C. and not less than 900° C.).
[3] Spinel: MgO.Al$_2$O$_3$

TABLE B3

| Sample No. | Element | Existence of heater | ΔA/F 3000 rpm* | 1000 rpm* |
|---|---|---|---|---|
| B35 | Sample No. B1 | Yes | 0.02 | 0.03 |
| B38 | Sample No. B3 | ↑ | 0.04 | 0.04 |
| B37 | Sample No. B12 | ↑ | 0.02 | 0.04 |
| B38 | Sample No. B20 | ↑ | 0.02 | 0.03 |
| B39 | Sample No. B23 | ↑ | 0.03 | 0.04 |
| B40 | Sample No. B29 | ↑ | 0.04 | 0.05 |
| B41 | Sample No. B32 | ↑ | 0.05 | 0.08 |
| Comparison BV | Comparison BII | ↑ | 0.09 | 0.13 |
| Comparison BVI | Sample No. B23 | No | 0.03 | 0.09 |

*The sensor temperature is 400° C. and 300° C. for 3000 rpm and 1000 rpm, respectively, with nonenergized heater, whereas rises by 100° C. or a little more when energized. Responsive property of sensor after test (msec).

TABLE B4

| | First protective layer | | Second protective layer | | | Difference in A/F ratio between the initial stage and after durability test | Responsive property of sensor after test (msec) | |
|---|---|---|---|---|---|---|---|---|
| | | | | IIa subgroup component[1] | | Initial control (Hz) | | |
| Sample No. | Metal oxide | Noble metal | Metal oxide | Composition | Amount (wt %) | | Rise | Fall |
| B42 | Al$_2$O$_3$ | — | Spinel | CaCl$_2$.2H$_2$O | 5 | 2.53 | 0.05 | 50 | 60 |
| B43 | ↑ | — | ↑ | CaCO$_3$ | 5 | 2.52 | 0.06 | 50 | 70 |
| Comparison BVII | ↑ | — | ↑ | — | — | 2.61 | 0.19 | 220 | 370 |
| B44 | ↑ | — | Al$_2$O$_3$ | CaCl$_2$.2H$_2$O | 15 | 2.63 | 0.05 | 50 | 70 |
| B45 | ↑ | — | TiO$_2$ | ↑ | 15 | 5.62 | 0.05 | 50 | 70 |
| B46 | ↑ | — | ↑ | CaCO$_3$ | 15 | 2.68 | 0.06 | 40 | 80 |

[1] The amount of the IIa subgroup component is relative to the metal oxide (spinel, Al$_2$O$_3$, TiO$_2$) of the second protective layer and converted into the IIa subgroup element (Ca, Mg).

TABLE B5

| Sample No. | First protective layer[2] | Second protective layer | | | Initial control (Hz) | A/F ratio difference between initial stage and after durability test | Response property after test (msec) | |
|---|---|---|---|---|---|---|---|---|
| | | Metal oxide | IIa subgroup component[1] Composition | Amount (wt %) | | | Rise | Fall |
| B47 | Semiconductor | Spinel | CaCl$_2$.2H$_2$O | 5 | 2.39 | 0.05 | 30 | 50 |
| B48 | ↑ | Spinel | ↑ | 10 | 2.25 | 0.05 | 30 | 50 |
| B49 | ↑ | Ti$_2$ | ↑ | 15 | 2.43 | 0.04 | 30 | 40 |
| B50 | ↑ | Al$_2$O$_3$ | MgCO$_3$ | 15 | 2.49 | 0.03 | 30 | 40 |
| Comparison BVIII | ↑ | — | — | — | 2.51 | 0.22 | 100 | 330 |

[1] The amount of the IIa subgroup component is relative to the metal oxide (spinel, TiO$_2$, Al$_2$O$_3$) of the second protective layer and converted into the IIa subgroup element (Ca, Mg)
[2] TiO$_2$ semiconductor also serves as the first protective layer.

What is claimed is:

1. An oxygen sensor for detecting oxygen concentration within an exhaust gas comprising a sensor element including a solid electrolyte, the sensor element having a protective layer formed thereon which is made of a heat-resistant metal oxide and which carries at least one silicon-reactive component selected from the group consisting of IIa subgroup elements in the international periodic table in a silicon-reactive state exclusive of oxides and silicon-reactive chlorides, carbonates and nitrates thereof and mixed compounds of said silicon-reactive chlorides, carbonates and nitrates on the side of the sensor element exposed to the exhaust gas, at least a part of said protective layer being formed of a nonstoichiometric compound of the heat-resistant metal oxide.

2. An oxygen sensor for detecting oxygen concentration in an exhaust gas comprising a sensor element including a solid electrolyte and a heater for heating the sensor element, the sensor element having a protective layer which is made of a heat-resistant metal oxide and which carries at least one silicon-reactive component selected from the group consisting of IIa subgroup elements in the international periodic table in a silicon-reactive state exclusive of oxides and silicon-reactive chlorides, carbonates and nitrates thereof and mixed compounds of said silicon-reactive chlorides, carbonates and nitrates on the side exposed to the exhaust gas of the oxygen sensor element, at least a part of said protective layer being present as a nonstoichiometric compound with respect to the heat-resistant metal oxide.

3. An oxygen sensor according to claim 1 or 2 wherein the protective layer also includes a noble metal at least in a part thereof.

4. An oxygen sensor for detecting oxygen concentration in an exhaust gas comprising a sensor element including a solid electrolyte having a protective layer which is made of a heat-resistant metal oxide and which carries at least one silicon-reactive component selected from the group consisting of IIa subgroup elements in the international periodic table in a silicon-reactive state exclusive of oxides and silicon-reactive chlorides, carbonates and nitrates thereof and mixed compounds of said silicon-reactive chlorides, carbonates and nitrates and a noble metal at the side exposed to the exhaust gas of the sensor element, at least a part of said protective layer being present as a nonstoichiometric compound with respect to the heat-resistant metal oxide, and a part of the protective layer in which said noble metal is carried being disposed closer to an electrode than a part of the protective layer in which said silicon-reactive component is carried.

5. An oxygen sensor for detecting oxygen concentration in an exhaust gas comprising a sensor element including a solid electrolyte and a heater for heating the sensor element, the sensor element having a protective layer which is made of a heat-resistant metal oxide and which carries at least one silicon-reactive component selected from the group consisting of IIa subgroup elements in the international periodic table in a silicon-reactive state exclusive of oxides and silicon-reactive chlorides, carbonates and nitrates thereof and mixed compounds of said silicon-reactive chlorides, carbonates and nitrates and a noble metal at the side exposed to the exhaust gas of the oxygen sensor element, at least a part of said protective layer being present as a nonstoichiometric compound with respect to the heat-resistant metal oxide, and a part of the protective layer in which said noble metal is carried being disposed closer to an electrode than a part of the protective layer in which said silicon-reactive component is carried.

6. An oxygen sensor according to claim 1, 2, 4 or 5, wherein the nonstoichiometric compound is titanium oxide which forms said protective layer, said IIa subgroup component being dispersed and carried by particles of the titanium oxide.

7. An oxygen sensor according to claim 1, 2, 4 or 5, wherein a main body of the sensor element is a solid electrolyte.

8. An oxygen sensor according to claim 1 or 2, wherein an inner protective layer not including the IIa subgroup component is provided on an inner side within said protective layer, said inner protective layer including a noble metal, and the surface directed to a measuring electrode of a main body of the sensor element has a roughness in a depth of not less than 10 μm.

9. An oxygen sensor according to claim 1, wherein the protective layer is formed of a first layer which neighbors the electrodes to directly protect the electrodes and which is made of a heat-resistant metal oxide, and a second layer which exists independently of the first layer and which comprises said IIa subgroup component.

10. An oxygen sensor according to claim 1, wherein the protective layer has a multiple layer structure including one layer made of spinel, alumina or mixtures thereof formed on the sensor element for protecting electrodes on the sensor element and a further layer including said silicon-reactive component provided at least on the outside of the one layer.

11. An oxygen sensor according to claim 10, wherein a noble metal is included in an amount not more than 5 wt % within the protective layer of spinel and/or alumina.

12. An oxygen sensor according to claims 9, 10, or 11 wherein a ceramic heater for heating the sensor element is provided.

13. An oxygen sensor according to claim 12, wherein the sensor element comprises a $ZrO_2$ solid electrolyte.

14. An oxygen sensor according to claim 4 or 5, wherein an inner protective layer not including the IIa subgroup component is provided on an inner side within said protective layer, said inner protective layer includes the noble metal, and the surface directed to a measuring electrode of a main body of the sensor element has a roughness in a depth of not less than 10 $\mu$m.

15. An oxygen sensor as defined in claim 1 wherein said heat-resistant metal oxide further comprises a stoichiometric compound of said heat-resistant metal-oxide so that the ratio of non-stoichiometric compound to the stoichiometric compound is not less than 3 to 2.

16. An oxygen sensor as defined in claim 1 wherein said heat-resistant metal oxide further comprises a stoichiometric compound of said heat-resistant metal oxide so that the ratio of non-stoichiometric compound to the stoichiometric compound is not less than 2 to 1.

17. An oxygen sensor for detecting oxygen concentration in an exhaust gas comprising an oxygen sensor element having a protective layer formed thereon which comprises at least one silicon-reactive component selected from the group consisting of IIa subgroup elements in the international periodic table in a silicon-reactive state exclusive of oxides and silicon-reactive chlorides, carbonates and nitrates thereof and mixed compounds of said silicon-reactive chlorides, carbonates and nitrates on the side of the oxygen sensor element exposed to the exhaust gas wherein a ceramic heater for heating the sensor element is provided, wherein the oxygen sensor element comprises an oxide semiconductor.

* * * * *